United States Patent [19]

Hildreth

[11] 4,299,779
[45] Nov. 10, 1981

[54] CATALYTIC REDUCTION OF 2-NITRONAPHTHALENE-4,8-DISULFONIC ACID AMMONIUM SALT

[75] Inventor: John D. Hildreth, Macclesfield, England

[73] Assignee: Clayton Aniline Co., Ltd., England

[21] Appl. No.: 216,491

[22] Filed: Dec. 15, 1980

[30] Foreign Application Priority Data

Feb. 16, 1980 [GB] United Kingdom ............... 05312/80

[51] Int. Cl.$^3$ ............................................. C07C 143/60
[52] U.S. Cl. .................................................. 260/508
[58] Field of Search ................................. 260/508, 510

[56] References Cited

FOREIGN PATENT DOCUMENTS 634 2/1979 European Pat. Off. ............ 260/508

*Primary Examiner*—Nicky Chan
*Attorney, Agent, or Firm*—Wenderoth, Lind & Ponack

[57] ABSTRACT

2-Naphthylamine-4,8-disulphonic acid is produced by catalytically hydrogenating the ammonium salt of 2-nitronaphthalene-4,8-disulphonic acid using Pt/C or Pd/C as the catalyst.

8 Claims, No Drawings

CATALYTIC REDUCTION OF 2-NITRONAPHTHALENE-4,8-DISULFONIC ACID AMMONIUM SALT

The present invention relates to the production of 2-naphthylamine-4,8-disulphonic acid.

2-Naphthylamine-4,8-disulphonic acid (C-acid) is an important starting material for the production of dyestuffs by diazotisation followed by coupling with various coupling components. It is normally made by aqueous Bechamp reduction of the corresponding nitro acid as its ammonium salt. While this process gives reasonably high yields of about 88%, the reduction period is prolonged. The reduction time is about 12 hours, and this is followed by a further approximate 20 hours for ashing out of iron, filtration and washing of iron sludge.

Attempts at catalytic hydrogenation of the nitro acid have been unsatisfactory, as large amounts of insoluble unknown impurity is formed. In addition, absorption of hydrogen quite frequently ceases very quickly, and catalyst poisoning is apparent.

Catalytic reduction of the nitro acid as its alkali metal salt has been described. While this process gives good results it means that the commonly available ammonium salt has to be converted to the alkali metal salt before the catalytic reduction is effected, causing some reduction in overall yield. Also the sodium salt is less soluble than the ammonium salt. The ammonium salt, as well as being more soluble than the sodium salt, also has a crystal form such that a more concentrated, stable and fluid slurry can be produced. This allows more of the nitro compound to be reduced in a given batch and thus increases the throughput.

Accordingly, the present invention provides a process for the manufacture of 2-naphthylamine-4,8-disulphonic acid which comprises catalytically hydrogenating the ammonium salt of 2-nitronaphthalene-4,8-disulphonic acid at superatmospheric pressure and a temperature of 60° to 150° C. as a solution or slurry in aqueous medium at a pH of 4.0 to 7.5, preferably 4.0 to 5.0, in the presence of a palladium/carbon or platinum/carbon catalyst.

The reaction is carried out at superatmospheric pressure, which may be from 15 to 1400 psi, preferably from 70 to 420 psi. The reaction temperature is preferably from 70° to 120° C.

The reaction is preferably carried out at a pH of 4.0 to 5.0. This may be achieved by first adjusting the pH to 6 with sodium hydroxide and then adding, e.g. acetic acid or sodium acetate, to bring the pH down to 4.0 to 5.0.

The Pd/C or Pt/C catalysts that are used may have a range of metal content, but preferably contain 0.5–10% by weight of Pd or Pt. The actual amount of catalyst used is chosen to give a reasonable rate of reaction, and may be such that the weight of Pd or Pt is 0.01 to 0.05% based on the weight of 2-nitronaphthalene-4,8-disulphonic acid.

The reaction is continued until consumption of hydrogen ceases. The time taken is dependent on the temperature and pressure used in the reactor and on the efficiency of the mixing during the reaction. The time of the reaction may be from 1 to 8 hours, but is often complete after 1–2 hours. After uptake of hydrogen ceases, it is preferred to maintain the reaction conditions for an additional time to ensure that the reaction is complete. The additional time may be up to 30 minutes.

While a Pt/C catalyst does not seem to be affected by any impurities present in the starting materials, a Pd/C catalyst is sometimes affected, and may result in the formation of considerable amounts of a yellow partially reduced intermediate. In such cases it is preferred to treat the 2-nitronaphthalene-4,8-disulphonic acid ammonium salt as a solution or slurry with active carbon before subjecting it to the catalytic hydrogenation.

The treatment may comprise heating the salt solution (or slurry) with 0.5 to 2.5% by weight of activated carbon at an elevated temperature, e.g. from 90° to 100° C. The time of treatment can be varied, depending on the amount of impurity present in the starting material. The time is normally not longer than 1 hour, with 30 minutes being sufficient in most cases.

The invention is illustrated by the following Examples in which parts by weight bear the same relationship to parts by volume as do kilograms to liters.

EXAMPLE 1

A shaking autoclave was charged with 80.0 parts by weight of 2-nitronaphthalene-4,8-disulphonic acid 100% mol. wt. 333 (charged as the ammonium salt filter cake) dissolved in 250 parts by volume water at 85°–90° C., the pH being carefully adjusted to 6.5–7.5 with sodium hydroxide solution, and the final reaction volume being 400 parts after further addition of water. To this was added 0.8 parts by weight of active carbon and the mass agitated for 30 minutes at 95°–100° C. 0.8 parts by weight of catalyst comprising 5% palladium on charcoal, as a 50% paste, was then added. The reactor was then closed, purged twice with hydrogen and then heated to 105°–110° C. With agitation, hydrogen was introduced at 140 psi and the conditions were maintained for 2 hours when consumption of hydrogen ceased.

The pressure was released and the catalyst filtered off at 90° C. 2-Naphthylamine-4,8-disulphonic acid was isolated from the filtrate in 94% theory yield and in good quality.

EXAMPLE 2

The process of Example 1 was repeated, except that the active carbon treatment was omitted, and 0.4 parts by weight of catalyst comprising 5% platinum on charcoal was used.

The reduction was effected in 2 hours, and the product was isolated as in Example 1, in 94% theory yield.

EXAMPLE 3

A shaking autoclave was charged with 160.0 parts by weight of 2-nitronaphthalene-4,8-disulphonic acid 100% mol. wt. 333 (charged as the ammonium salt filter cake) as a uniform aqueous slurry at pH 6.5–7.5 and 40% w/v concentration, i.e. final reaction volume 400 parts.

To this was added 0.8 parts by weight of active carbon and the mass agitated for 30 minutes at 95°–100° C. 1.6 parts by weight of catalyst comprising 5% palladium on charcoal, as a 50% paste, was then added. The reactor was then closed, purged twice with hydrogen and then heated to 110°–115° C. With agitation, hydrogen was introduced at 140 psi and the conditions were maintained for 3 hours when consumption of hydrogen ceased. 2-Naphthylamine-4,8-disulphonic acid of good quality was isolated in 94% theory yield (136 parts mol. wt. 303).

EXAMPLE 4

A shaking autoclave was charged with 200.0 parts by weight water and 80.0 parts by weight of 2-nitronaphthalene-4,8-disulphonic acid (as the ammonium salt filter cake). The mixture was heated to 90°–95° C. and the pH adjusted first to 6.0 with sodium acetate solution and then to 4.5 with acetic acid.

0.8 Parts by weight active carbon were added and the mixture maintained for 30 minutes at 90°–95° C.

The mixture was then cooled to 70°–75° C. and 0.8 parts by weight of catalyst comprising 5% palladium on charcoal, as a 50% paste, added. The mixture was hydrogenated at a temperature of 70°–75° C. and 140 psi pressure. The reduction was completed in 1½ hours and the product was obtained in 95% theory yield.

I claim:

1. A process for the manufacture of 2-naphthylamine-4,8-disulphonic acid which comprises catalytically hydrogenating the ammonium salt of 2-nitronaphthalene-4,8-disulphonic acid at superatmospheric pressure and a temperature of 60° to 150° C. in aqueous medium at a pH in the range 4.0–7.5, in the presence of a platinum/carbon or palladium/carbon catalyst.

2. A process as claimed in claim 1, in which the catalyst is palladium/carbon and the ammonium salt is subjected to a pre-treatment with activated carbon before being hydrogenated.

3. A process as claimed in claim 2, in which the pre-treatment comprises heating with 0.5 to 2.5% by weight of activated carbon at a temperature of from 90° to 100° C.

4. A process as claimed in claim 1, in which the hydrogenation is carried out at a pressure of from 15 to 1400 p.s.i.

5. A process as claimed in claim 4, in which the pressure is from 70 to 420 p.s.i.

6. A process as claimed in claim 1, in which the hydrogenation is carried out at a temperature of from 70° to 120° C.

7. A process as claimed in claim 1, in which the amount of catalyst is such that the weight of Pt or Pd is 0.01 to 0.05% based on the weight of 2-nitronaphthalene-4,8-disulphonic acid.

8. A process as claimed in claim 1, in which the hydrogenation is carried out at a pH of 4.0–5.0.

* * * * *